United States Patent [19]

Woolard et al.

[11] Patent Number: 5,266,701
[45] Date of Patent: Nov. 30, 1993

[54] PROCESS FOR PRODUCTION OF 2-IMINOTHIAZOLIDINES AND OXAZOLIDINES

[75] Inventors: Frank X. Woolard, Richmond; Charles Kezerian, Orinda, both of Calif.

[73] Assignee: ICI Americas Inc., Wilmington, Del.

[21] Appl. No.: 989,574

[22] Filed: Mar. 7, 1990

Related U.S. Application Data

[63] Continuation of Ser. No. 214,349, Jul. 1, 1988, abandoned.

[51] Int. Cl.$^5$ .................. C07D 263/28; C07D 277/18
[52] U.S. Cl. .................................... 548/199; 548/233
[58] Field of Search ......................... 549/233, 199

[56] References Cited

U.S. PATENT DOCUMENTS 2,186,894  1/1940  Brodersen et al. ............... 548/233
4,665,083  5/1987  Lempert et al. ................. 548/233

OTHER PUBLICATIONS

Matveev et al., Chemical Abstracts, vol. 76, No. 153651g (1972).
Migrdichian "Organic Cyanogen Compounds", pp. 116–118 (1947).
March, Advanced Organic Chemistry pp. 316–317 (1985).

*Primary Examiner*—Robert Gerstl
*Attorney, Agent, or Firm*—Joel G. Ackerman

[57] ABSTRACT

Compounds having the formula

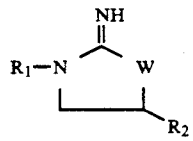

in which $R_1$ is optionally substituted phenyl, $R_2$ is $C_1$-$C_4$ alkyl or $C_1$-$C_4$ haloalkyl and W is oxygen or sulfur are produced by reaction of a corresponding phenyl cyanamide with an epoxide or episulfide in the presence of a base and optionally a solvent.

11 Claims, No Drawings

PROCESS FOR PRODUCTION OF 2-IMINOTHIAZOLIDINES AND OXAZOLIDINES

This is a continuation, of application Ser. No. 214,349, filed Jul. 1, 1988, now abandoned.

BACKGROUND AND PRIOR ART

This invention is for a process for production of 5-(alkyl or haloalkyl)-2-iminooxazolidines and thiazolidines. These compounds may be represented by the general formula

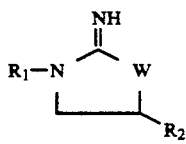

in which $R_1$ represents an optionally substituted phenyl ring, $R_2$ is $C_1$-$C_4$ alkyl or $C_1$-$C_4$ haloalkyl and W is oxygen or sulfur. Compounds of this general type have been described in the prior art, for instance in U.S. Pat. No. 4,665,083 (iminothiazolidines) and a paper by Mateev et al., Chemical Abstracts, Vol. 76, No. 153651 g (1972) (production of 2-imino-3-phenyl-5-chloromethyl-1,3-oxazolidine). Iminothiazolidines of this type are also disclosed as intermediates for substituted 2-iminothiazolidines in U.S. patent applications Nos. 214,348 and 214,347 of Frank X. Woolard, entitled "2-(Acylimino)thiazolidine Herbicides" and "Novel Herbicidal 2-Sulfonyliminothiazolidines", filed concurrently herewith.

U.S. Pat. No. 4,665,083 discloses a number of processes for preparing such compounds including cyclization of an isocyanate, cyclization of a thiourea, and reaction of an iminothiazolidine with an aromatic fluoride. Mateev et al. disclose reaction of phenyl cyanamide with epichlorohydrin to produce a nearly 50/50 mixture of 2-imino-3-phenyl-5-chloromethyl-1,3-oxazolidine and 2-N-phenylimino-5-chloromethyl-1,3-oxazolidine, as well as corresponding butyl compounds produced from butyl cyanamide.

SUMMARY OF THE INVENTION

This invention comprises a process for the production of compounds having the formula

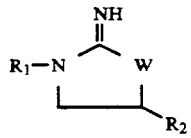

in which $R_1$ is an optionally substituted phenyl group, $R_2$ is $C_1$-$C_4$ alkyl or $C_1$-$C_4$ haloalkyl, and W is oxygen or sulfur comprising reacting an optionally substituted phenyl cyanamide having the formula

$R_1NHCN$ with a compound having the formula

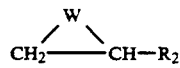

in the presence of a base.

DETAILED DESCRIPTION OF THE INVENTION

According to the invention, an optionally substituted phenyl cyanamide having the formula

$R_1NHCN$ is reacted with an epoxide or episulfide of the formula

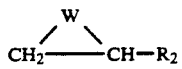

to produce the desired product.

The phenyl group corresponding to designation $R_1$ may be unsubstituted, or mono- or poly-substituted.

In one embodiment the phenyl group has the general formula

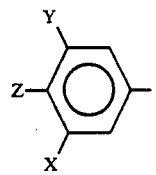

in which

X is hydrogen, halogen, nitro, cyano, perhalomethyl, difluoromethyl, pentafluoroethyl, $C_1$-$C_4$ alkyl, $C_1$-$C_4$ alkoxy, trifluoromethylthio, trifluoromethoxy, difluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$-$C_4$ alkyloximinomethyl, benzyloximinomethyl, 1-($C_1$-$C_4$ alkyl)oximinoethyl and 1-benzyloximinoethyl;

Y is hydrogen, halogen, nitro, cyano, perhalomethyl, difluoromethyl, pentafluoroethyl, $C_1$-$C_4$ alkyl, $C_1$-$C_4$ alkoxy, trifluoromethylthio, trifluoromethoxy, tetrafluoroethoxy, methylsulfonyl and trifluoromethylsulfonyl; and Z is hydrogen or fluoro if Y is hydrogen, or hydrogen if Y is other than hydrogen.

Examples of such cyanamides are phenyl cyanamide, m-trifluoromethylphenyl cyanamide, m-chlorophenyl cyanamide, m-cyanophenyl cyanamide, m-nitrophenyl cyanamide, 3-chloro-4-fluorophenyl cyanamide, and 3-trifluoromethyl-4-fluorophenyl cyanamide. The cyanamides may be obtained commercially, or if not commercially available may be readily synthesized by a process such as described in Organic Synthesis Col., Vol. IV, p. 172.

The epoxides or episulfides utilized in this process have the general formula

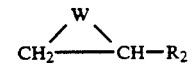

in which W is oxygen or sulfur and $R_2$ is $C_1$-$C_4$ alkyl or $C_1$-$C_4$ haloalkyl. Most preferably, $R_2$ is methyl, ethyl or chloromethyl. These compounds may be obtained commercially, or if not readily available, may be synthesized by conventional methods.

The reaction between the starting materials phenyl cyanamide and epoxide or episulfide is generally conducted at a temperature of about 25° C. to about 120° C., preferably from about 80° C. to about 110° C. in the presence of a base. Preferably the base is used in stoichiometric amounts with respect to the starting materials but in general the amount of the base may range from about 50 to about 150 mole percent with respect to the starting phenyl cyanamide. Preferably, the base is a moderate strength base, that is, a substance which acts as a base but whose strength or activity as a base lies between that of strong bases such as alkali metal hydroxides and weak bases such as bicarbonates. Moderate bases suitable for use in this process include inorganic bases such as alkali metal carbonates and organic bases such as tertiary amines. A preferred base for this process is potassium carbonate.

Preferably the process is conducted in the presence of a solvent, most preferably an aprotic solvent, such as toluene, methyl ethyl ketone, benzene, tetrahydrofuran or p-dioxane.

In general, there are two possible cyclic products,

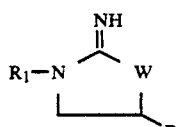
(I)

and

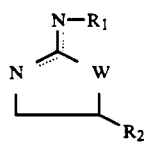
(II)

both types of which were produced (in nearly equal amounts) and isolated in the process of Matveev. In contradistinction, only the 2-imino-3-phenyl-5-substituted type (I) is produced and isolated by the procedure described herein. The presence of the second type (II) of cyclic product, which can exist in two tautomeric forms (2-phenylimino oxa- or thiazolidine or 2-phenylamino oxa- or thiazoline), shown by the dotted lines, was not detected in either the crude reaction mixture (by capillary gas chromatography) or the final product (by spectral methods).

The conduct of this process is further illustrated by the following examples.

EXAMPLE I

Production of 2-Imino-3-phenyl-5-ethyl-1,3-oxazolidine

In a flask were combined 3.0 grams (g) (25.4 mmol) phenyl cyanamide, 1.83 g (25.4 mmol) 1,2-epoxy butane, 3.51 g (25.4 mmol) potassium carbonate and 50 milliliters (ml) methyl ethyl ketone. The mixture was stirred overnight under a nitrogen blanket at room temperature. It was then filtered and the methyl ethyl ketone removed in vacuo. The solids recovered from the filter were extracted with acetone and combined with the residue from the main portion. The combined solids were dissolved in water and extraced with 15% isopropanol in chloroform. The solvents were removed in vacuo producing 2.30 g (48% of theoretical yield) of the desired product. Spectroscopic analysis confirmed the structure of the desired product. No type II product was detected.

EXAMPLE II

Production of 2-Imino-3-(3-trifluoromethyl)phenyl-5-ethyl-1,3-thiazolidine

In a flask were combined 62.24 g (0.334 mol) 3-trifluoromethylphenyl cyanamide, 29.48 g (0.334 mol) 1,2-butane episulfide, 46.16 g (0.334 mol) potassium carbonate and 500 ml methyl ethyl ketone. The mixture was heated with stirring under reflux for 3 hours, then cooled to room temperature and filtered. The solvent was removed, producing a cloudy oil which was dissolved in ethyl acetate and washed with water and saturated sodium chloride. The washed liquid was dried and the solvent was again removed in vacuo. There was obtained 73.99 g (81% of theoretical yield) of the desired product, a clear yellow oil. The structure of the product was confirmed by spectroscopy. No type II product was detected.

EXAMPLE III

Production of 2-Imino-3-(3-chloro-4-fluoro)phenyl-5-ethyl-1,3-thiazolidine

There were combined in a flask 13.20 g (77.4 mmol) 3-chloro-4-fluorophenyl cyanamide, 10.70 g (77.4 mmol) potassium carbonate and 150 ml methyl ethyl ketone. The resulting suspension was stirred and heated to refluxing. Then 6.82 g (77.4 mmol) 1,2-butane episulfide was added in one portion, and the stirring under reflux continued. After reaction was complete the mixture was filtered and the solvent removed. The residue, a deep purple oil, was dissolved in ethyl acetate, washed with water, dried over magnesium sulfate, and the solvent again removed under vacuum. The purple residue was dissolved in a mixture of diethyl ether and ethyl acetate. A stream of gaseous hydrogen chloride was introduced into the liquid layer. The precipitated hydrochloride salt was filtered, washed with ether and partitioned between 1:1:1 saturated potassium carbonate/water/diethyl ether. The ether layer was separated and the aqueous layer washed again with ether. The combined organic phases were dried and the solvent removed under vacuum to give 6.43 g (32% of theoretical yield) of the desired product, a pale purple oil. Structure was confirmed by spectroscopic analyses. No type II product was detected.

EXAMPLE IV

Production of 2-Imino-3-(3-cyano)phenyl-5-ethyl-1,3-thiazolidine

Similarly to Example III, this product was produced from 3-cyanophenyl cyanamide, 1,2-butane episulfide, and potassium carbonate. The yield was 31% of theoretical. The structure was confirmed as before; no type II product was detected.

EXAMPLE V

Production of 2-Imino-3-(3-chloro)phenyl-5-ethyl-1,3-thiazolidine

The above compound was prepared similarly to Example III from 3-chlorophenyl cyanamide, 1,2-butane episulfide and potassium carbonate. The yield was 71% of theoretical, a yellow-brown oil. The product structure was confirmed by analyses; no type II product was detected.

EXAMPLE VI

Production of 2-Imino-3-(3-trifluoromethyl-4-fluoro)phenyl-5-ethyl-1,3-thiazolidine Similarly to Example III, this compound was produced from 3-trifluoromethyl-4-fluorophenyl cyanamide, 1,2-butane episulfide and potassium carbonate. The yield was 38% of theoretical (a yellow oil). The structure of the product was confirmed by spectroscopy; no type II product was detected.

Modifications and variations of this process may be apparent to those skilled in the art. The invention, however, is not limited to the examples above but only by the claims which follow.

What is claimed is:

1. A process for the production of 2-iminothiazolidines or oxazolidines having the formula

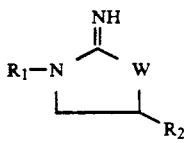

in which $R_1$ is optionally substituted phenyl, $R_2$ is $C_1$-$C_4$ alkyl or $C_1$-$C_4$ haloalkyl, and W is oxygen or sulfur, comprising reacting an optionally substituted phenyl cyanamide having the formula $$R_1NHCN \qquad (II)$$

with a compound having the formula

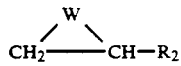

in which $R_1$, $R_2$ and W are as above defined, in the presence of a moderate strength base.

2. A process according to claim 1 further conducted in the presence of a solvent.

3. A process according to claim 2 in which the solvent is an aprotic solvent.

4. A process according to claim 1 conducted at a temperature of about 25° C. to about 120° C.

5. A process according to claim 2 conducted at the reflux temperature of the solvent.

6. A process according to claim 1 in which W is oxygen.

7. A process according to claim 1 in which W is sulfur.

8. A process according to claim 1 in which $R_2$ is methyl, ethyl or chloromethyl.

9. A process according to claim 1 in which $R_1$ is

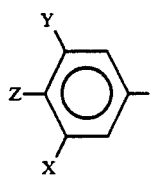

in which

X is hydrogen, halogen, nitro, cyano, perhalomethyl, difluoromethyl, pentafluoroethyl, $C_1$-$C_4$ alkyl, $C_1$-$C_4$ alkoxy, trifluoromethylthio, trifluoromethoxy, difluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$-$C_4$ alkyloximinomethyl, benzyloximinomethyl, 1-($C_1$-$C_4$ alkyl)oximinoethyl and 1-benzyloximinoethyl;

Y is hydrogen, halogen, nitro, cyano, perhalomethyl, difluoromethyl, pentafluoroethyl, $C_1$-$C_4$ alkyl, $C_1$-$C_4$ alkoxy, trifluoromethylthio, trifluoromethoxy, tetrafluoroethoxy, methylsulfonyl and trifluoromethyl -sulfonyl; and Z is hydrogen or fluoro if Y is hydrogen, or hydrogen if Y is other than hydrogen.

10. A process according to claim 1 comprising selectively producing a compound of formula (I).

11. A process according to claim 1 conducted in the presence of an aprotic solvent.

* * * * *